United States Patent
Nakamoto et al.

(10) Patent No.: US 8,197,524 B2
(45) Date of Patent: Jun. 12, 2012

(54) ENERGY IRRADIATION DEVICE AND METHOD, CONTROL DEVICE AND CONTROL METHOD

(75) Inventors: Ryo Nakamoto, Tokyo (JP); Hiroshi Shiono, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1664 days.

(21) Appl. No.: 11/525,032

(22) Filed: Sep. 22, 2006

(65) Prior Publication Data
US 2007/0179572 A1    Aug. 2, 2007

(30) Foreign Application Priority Data
Sep. 30, 2005   (JP) ................................. 2005-286897

(51) Int. Cl.
*A61F 7/00*    (2006.01)
(52) U.S. Cl. ............. 607/96; 607/89; 607/100; 607/102
(58) Field of Classification Search .............. 606/10–12, 606/27–31; 607/88–92, 96–102; 600/437–439, 600/476–480
See application file for complete search history.

(56) References Cited

U.S. PATENT DOCUMENTS

| | | | |
|---|---|---|---|
| 4,638,436 A * | 1/1987 | Badger et al. ................. 607/102 |
| 6,047,080 A * | 4/2000 | Chen et al. ..................... 382/128 |
| 6,358,246 B1 * | 3/2002 | Behl et al. ........................ 606/34 |
| 6,488,697 B1 | 12/2002 | Ariura et al. |
| 7,060,061 B2 * | 6/2006 | Altshuler et al. .................. 606/3 |
| 7,217,266 B2 * | 5/2007 | Anderson et al. ................ 606/12 |
| 7,713,294 B2 * | 5/2010 | Bornstein ........................ 607/88 |

FOREIGN PATENT DOCUMENTS

| | | |
|---|---|---|
| JP | 7-116274 | 5/1995 |
| JP | 2001-046389 A | 2/2001 |
| JP | 2001-079015 A | 3/2001 |
| JP | 2002-514480 | 5/2002 |
| WO | WO 99/58194 | 11/1999 |

\* cited by examiner

*Primary Examiner* — Ahmed Farah
(74) *Attorney, Agent, or Firm* — Buchanan Ingersoll & Rooney PC (57) ABSTRACT

An energy irradiation device for medical use to irradiate a living body with energy includes a data storage for storing data indicative of correlations between information about bloodstream quantities and amounts of tissue necrosed in living bodies for a plurality of living bodies differing in bloodstream quantity that are irradiated with a predetermined quantity of the energy, a calculation unit for calculating a quantity of the energy with which to irradiate a predetermined living body based on the data stored in the data storage, the information about the bloodstream quantity in the predetermined living body, and the amount of tissue to be necrosed in the predetermined living body.

12 Claims, 12 Drawing Sheets

|  | FIG.4A | FIG.4B | FIG.4C |
|---|---|---|---|
| BLOOD VESSEL DISTRIBUTION DENSITY (PIECES/10mm$^2$) | 122 | 226 | 408 |
| NECROSIS AREA (mm$^2$) | 15 | 10 | 0 |

|  | FIG.9A | FIG.9B | FIG.9C |
|---|---|---|---|
| BLOOD VESSEL DISTRIBUTION DENSITY (PIECES/10mm$^2$) | 122 | 226 | 408 |
| NECROSIS AREA (mm$^2$) | 15 | 10 | 0 |

ENERGY IRRADIATION DEVICE AND METHOD, CONTROL DEVICE AND CONTROL METHOD

FIELD OF THE INVENTION

The present invention generally relates to the irradiation of living body tissue. More particularly, the invention pertains to an energy irradiation device for thermal therapy of a tissue in a living body by irradiation with energy such as laser light, microwave, radio wave, ultrasonic wave, and hyperthermia.

BACKGROUND DISCUSSION

Known energy irradiation devices for medical use include an elongate insertion portion inserted into a living body by utilizing a body lumen or through a small incision. Living body tissue, including a lesion portion, is irradiated with energy such as laser light, microwave, radio wave, and ultrasonic wave from the insertion portion, to cause annihilation of the tissue at the lesion portion through degeneration, necrosis, coagulation, cauterization or transpiration.

The energy irradiation devices are generally used to cure a lesion portion located in or in the vicinity of a skin layer of a living body tissue by irradiating the lesion portion directly with energy. These devices are also utilized for thermal therapy of a lesion portion located in a deep part of a living body tissue, such as the prostate.

In thermal therapy of the lesion portion located in a deep part of a living body tissue, it is important for the lesion portion to be heated at an appropriate temperature. To heat the lesion portion at a desired temperature, energy irradiation devices used in the past for this purpose have been designed to measure the temperature of the irradiated portion (the position of the skin portion of a living body on which the energy is incident, in the case of radiating the energy toward the lesion portion located in a deep part) and to control the output of the energy so that the measured temperature of the irradiated portion will be the desired temperature. An example is disclosed in Japanese Patent Laid-open No. Hei 7-116274 and JP-A-2002-514480 (WO 99/58194).

SUMMARY

It is known, however, that even if the output of the energy is controlled so that the temperature of the irradiated portion will be a desired temperature, the effect of the thermal therapy will differ from patient to patient. It has been found that the reason is because even if the heating is controlled so that the temperature of the irradiated portion is brought to the desired temperature, the lesion portion located at a deep part is not necessarily heated at the appropriate temperature, and the temperature at the lesion portion depends on variations in living body tissues from patient to patient.

In general, the energy entering from the irradiated portion passes through blood vessel tissue or the like in the living body before reaching the lesion portion. In this case, the blood flowing in the blood vessel is warmed by the energy propagating therethrough, and the blood thus warmed is immediately carried away to other positions in the blood vessel. In short, during thermal therapy of a lesion portion located at a deep part, the blood vessel tissue located at a position through which the energy propagates acts as a heat draining element.

Ordinarily, factors or values relating to the so-called bloodstream quantity, such as blood amount, blood vessel distribution and blood flow rate, which determine the blood vessel tissue differ from person to person, and so the effect of the blood vessel tissue acting as a heat draining element differs from person to person. For example, the heat draining action is comparatively strong under conditions where the blood amount is relatively large, the blood vessel distribution density is relatively high, and/or the blood flow rate is relatively high. On the other hand, the heat draining action is comparatively weak under conditions where the blood amount is relatively small, the blood vessel distribution density is relatively low, and/or the blood flow rate is relatively low.

Thus, in the known devices which utilize energy output control based on the temperature at the irradiated portion, it is difficult if not impossible to avoid the problem that the lesion portion may not be heated at an appropriate temperature and the effect of thermal therapy is scattered due to variations in the blood vessel tissue of the living body from patient to patient.

According to one aspect of the disclosed subject matter, a method of irradiating a predetermined living body with energy involves inputting into an energy irradiating device bloodstream quantity information indicating a bloodstream quantity in a predetermined living body to be irradiated, determining a quantity of energy with which to irradiate the predetermined living body based on the inputted bloodstream quantity information, and irradiating the predetermined living body with the determined quantity of energy through operation of the energy irradiating device.

According to another aspect, a method of irradiating a predetermined living body with energy comprises determining a quantity of energy with which to irradiate a predetermined living body based on stored data providing correlations between information about bloodstream quantities and an amount of tissue necrosed in different living bodies differing in bloodstream quantity that are irradiated with a predetermined quantity of the energy, information about the bloodstream quantity of the predetermined living body, and an amount of tissue to be necrosed in the predetermined living body. The predetermined living body is irradiated with the determined quantity of energy.

An energy irradiation device for medical use to irradiate a living body with energy comprises storage means for storing data providing correlations between information about bloodstream quantities and an amount of tissue necrosed in different living bodies differing in bloodstream quantity that are irradiated with a predetermined quantity of the energy, and calculation means for calculating the quantity of the energy with which to irradiate a predetermined living body based on the data stored in the storage means, information about the bloodstream quantity in the predetermined living body, and an amount of tissue to be necrosed in the predetermined living body.

A control device connected to an energy irradiation device for irradiating a living body with energy to control a quantity of the energy outputted fro the energy irradiation device comprises storage means for storing data indicating correlations between information about bloodstream quantities and amounts of tissue necrosed in living bodies for a plurality of living bodies differing in bloodstream quantity that are irradiated with a predetermined quantity of the energy, and calculation means for calculating a quantity of the energy with which to irradiate a predetermined living body based on the data stored in the storage means, information about the bloodstream quantity in the predetermined living body, and the amount of tissue to be necrosed in the predetermined living body.

According to the disclosure here, the energy irradiation device permits thermal therapy of a lesion portion, for example a lesion portion located at a deep part of a living body, by which the lesion portion can be heated at an appropriate temperature regardless of variations in the blood vessel tissue of the living body from patient to patient.

DETAILED DESCRIPTION

Various embodiments of the energy irradiation device, control device and control method as disclosed herein are described in detail below with reference to the accompanying drawing figures. The following detailed description describes the use of laser light as an example of the energy used for thermal therapy. However, it is to be understood that the disclosure is not limited in that regard as other forms of energy as appropriate can be employed including, for example, microwave, radio wave, ultrasonic wave and hyperthermia.

1. Energy Irradiation Device

Figure 1:
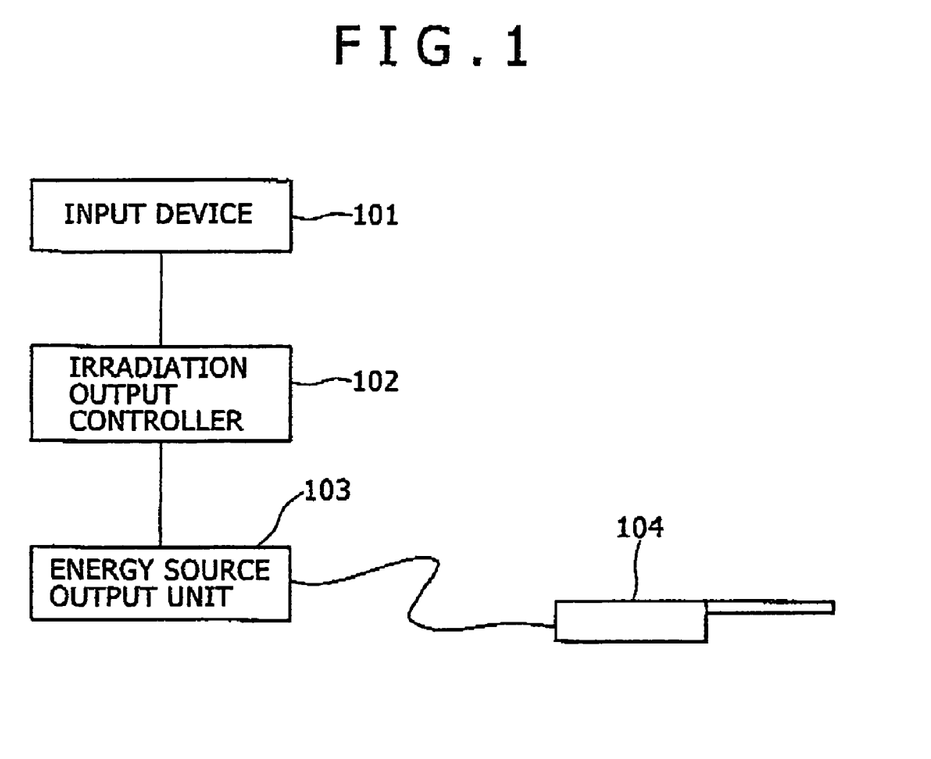
FIG. 1 is a schematic illustration of features forming the energy irradiation device disclosed herein according to a first embodiment.

FIG. 1 is a schematic illustration of the general configuration (the configuration for illustrating mainly the flow of a control signal) of an energy irradiation device according to one disclosed embodiment.

The energy irradiation device includes an input device 101 for inputting a blood vessel distribution density of a living body and a target necrosis area in the living body. An irradiation output controller 102 calculates or determines the energy quantity of the energy (for example, laser light) for irradiation therewith, and the energy quantity is obtained based on a value (specifically, a target temperature at an irradiated portion) calculated or determined by use of, for example, a blood vessel distribution density inputted from the input device 101. An energy source output unit 103 outputs the energy according to the energy quantity obtained or calculated by the irradiation output controller 102. An emission unit 104 emits, toward a living body, the energy outputted from the energy source output unit 103.

2. Emission Unit

Figure 2:
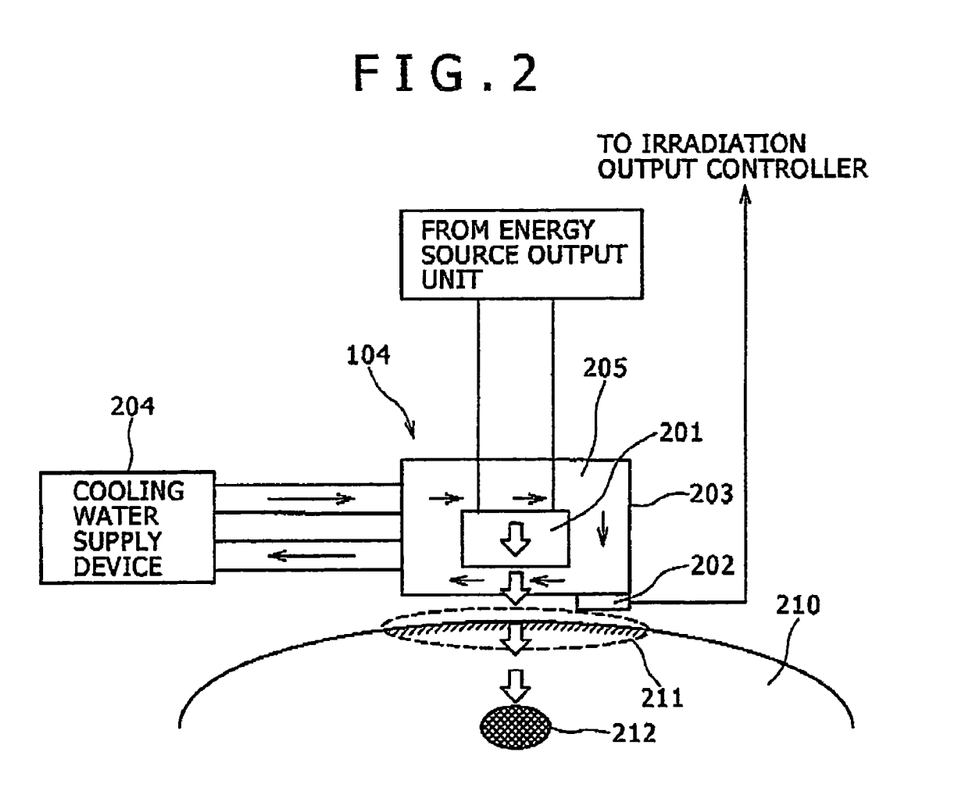
FIG. 2 is a schematic illustration of the emission unit 104 forming a part of the energy irradiation device according to the first embodiment.

The general configuration of the emission unit 104 according to one embodiment is illustrated in FIG. 2. The emission unit 104 includes an emission port 201 through which the energy outputted from the energy source output unit 103 is actually emitted toward a lesion portion 212 of a living body 210. The emission port 201 is surrounded by a housing 203, and cooling water 205 is circulated between the emission port 201 and the housing 203. This helps ensure that the irradiated portion 211 of the living body 210 which is in contact with the housing 203 is cooled and thus protected from thermal injury. A cooling water supply device 204 is connected to the housing 203 of the emission unit 104 so as to supply the cooling water 205 to the area between the emission port 201 and the housing 203.

The emission unit 104 also includes a temperature sensor 202 (temperature measuring means) which measures the temperature at the irradiated portion 211 and outputs the measurement result to the irradiation output controller 102. In the illustrated embodiment, the temperature sensor 202 is mounted on the housing 203 at a position facing the living body during use.

3. Irradiation Output Controller

Figure 3:
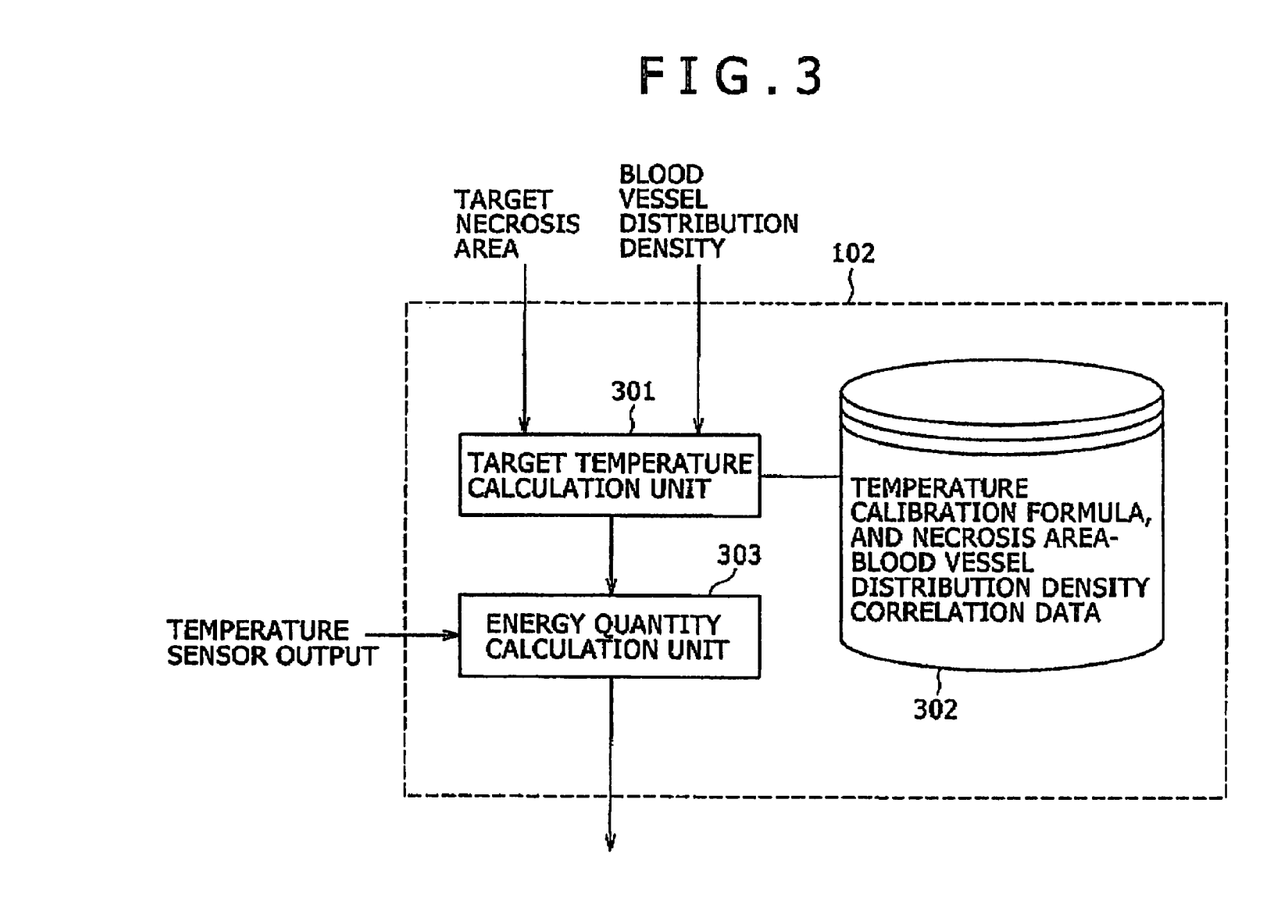
FIG. 3 is a schematic illustration of features forming the irradiation output controller 102 of the energy irradiation device according to the first embodiment.

FIG. 3 illustrates features associated with the irradiation output controller 102 forming a part of the energy irradiation device. The irradiation output controller 102 includes a target temperature calculation unit 301 (target temperature calculation means) which calculates a temperature to be used as a target in determining the temperature to which the irradiated portion 211 (shown in FIG. 2) should be brought by controlling the output of the energy. The target temperature calculation unit 301 calculates the target temperature for the irradiated portion 211 based on the target necrosis area and the blood vessel distribution density which are inputted and with reference to a "temperature calibration formula" and "necrosis area-blood vessel distribution density correlation data" which are stored in data storage 302 (storage means) such as a hard disk. Details associated with the calculation method will be described in more detail below. The target necrosis area and the blood vessel distribution density are inputted to the irradiation output controller 102 through the input device 101 by the operator to be used in the target temperature calculation unit 301.

An energy calculation unit 303 (energy quantity calculation means) calculates or determines the quantity of energy to be outputted (the wattage of the driving voltage and the irradiation time, in the example where the energy is laser light), based on the target temperature (target value) for the irradiated portion calculated in the target temperature calculation unit 301 and the temperature (measured value) outputted from the temperature sensor 202.

4. Calculation Method in Target Temperature Calculation Unit

The description below describes an example of a calculation method for calculating the target temperature in the target temperature calculation unit 301.

4.1 Relationship between Blood Vessel Distribution Density and Necrosis Area

Figure 4A:
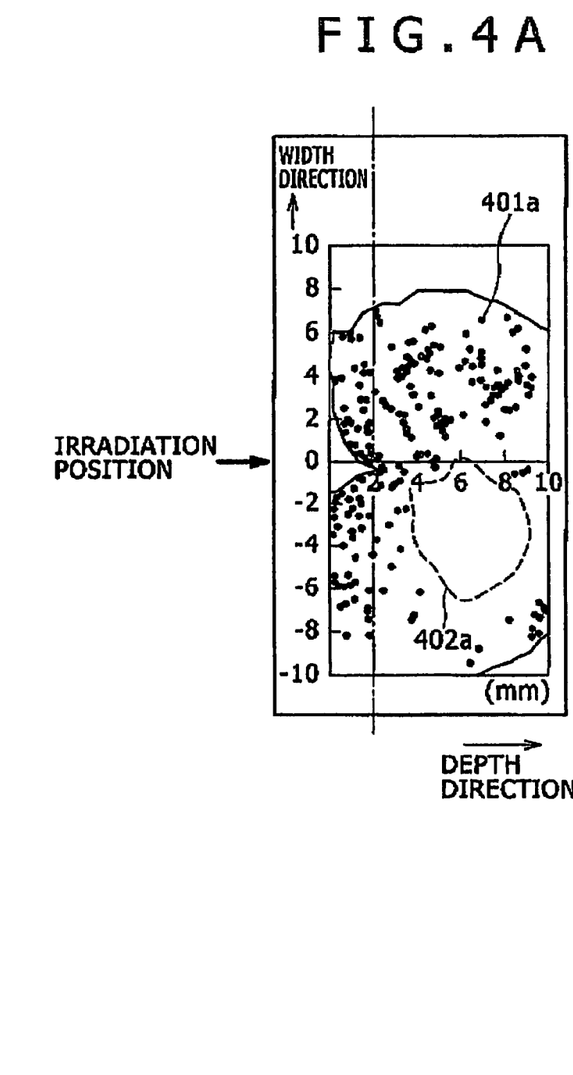
FIGS. 4A-4C are diagrams visualizing the correlation between blood vessel distribution density and necrosis area, during irradiation with laser light while controlling the laser output so that the temperature at the irradiated portion of a living body will be 34° C.
Figure 4B:
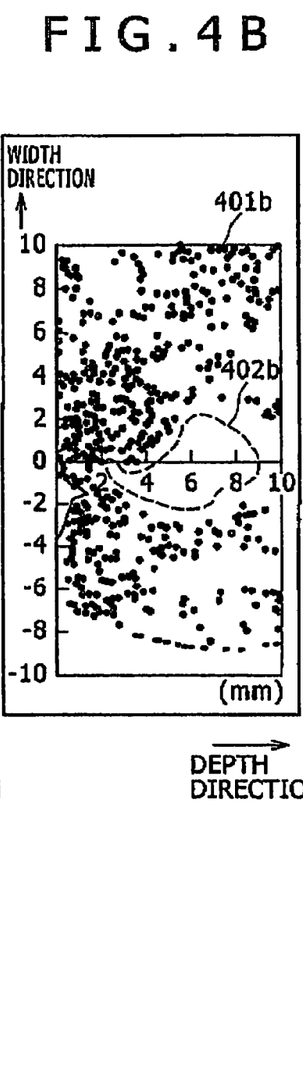
Figure 4C:
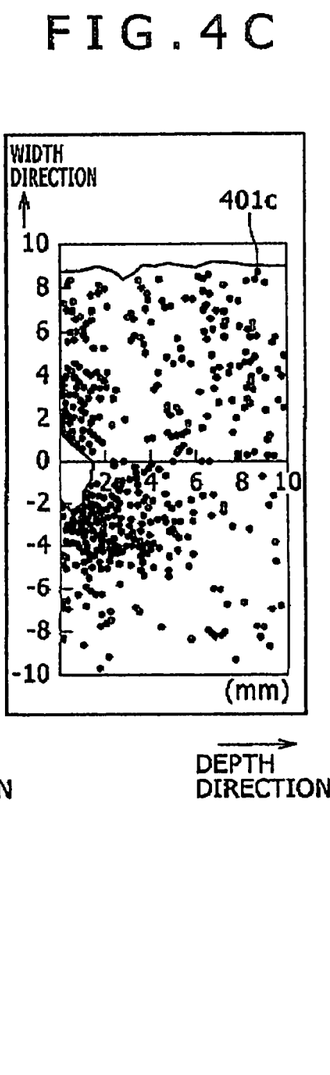

FIGS. 4A-4C are diagrams visualizing the relationship between the blood vessel distribution density and necrosis area while irradiating with laser light while controlling the output so that the temperature of the irradiated portion of the living body will be 34° C.

In FIGS. 4A-4C, the solid circles designated as examples as 401a-401c represent blood vessels, and the blood vessel distribution density increases in the direction from FIG. 4A toward FIG. 4C. Reference characters 402a and 402b denote the portions necrosed by irradiation with laser light. Specifically, FIG. 4A shows an example where the irradiation with laser light was conducted while controlling the output so that the irradiated portion of a living body having a low blood vessel distribution density would be at a temperature of 34° C., with the result that the portion denoted by 402a was necrosed. On the other hand, FIG. 4C shows a case where the irradiation with laser light was conducted while controlling the output so that the irradiated portion of a living body having a high blood vessel distribution density would be 34° C., with the result that no portion was necrosed. Further, FIG. 4B shows a case where the irradiation with laser light was conducted while controlling the output so that the irradiated portion of a living body having an intermediate level of blood vessel distribution density would be 34° C., with the result that the portion denoted by 402b was necrosed.

It is thus understood from the illustrations in FIGS. 4A-4C that even if the output of laser light is so controlled that the temperature of the irradiated portion is at a predetermined temperature, the effect of the thermal therapy (the size or extent, if any, of the necrosis area) differs relatively significantly based on differences in the blood vessel distribution density of the living body.

Figure 5A:
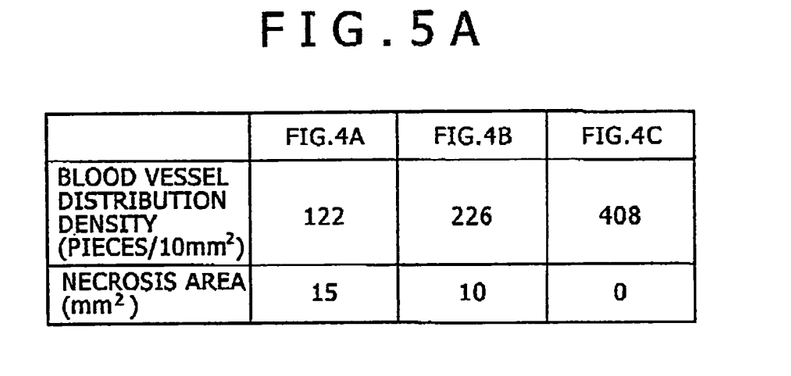
FIGS. 5A and 5B set forth in a table and a graph respectively the correlation between blood vessel distribution density and necrosis area.
Figure 5B:
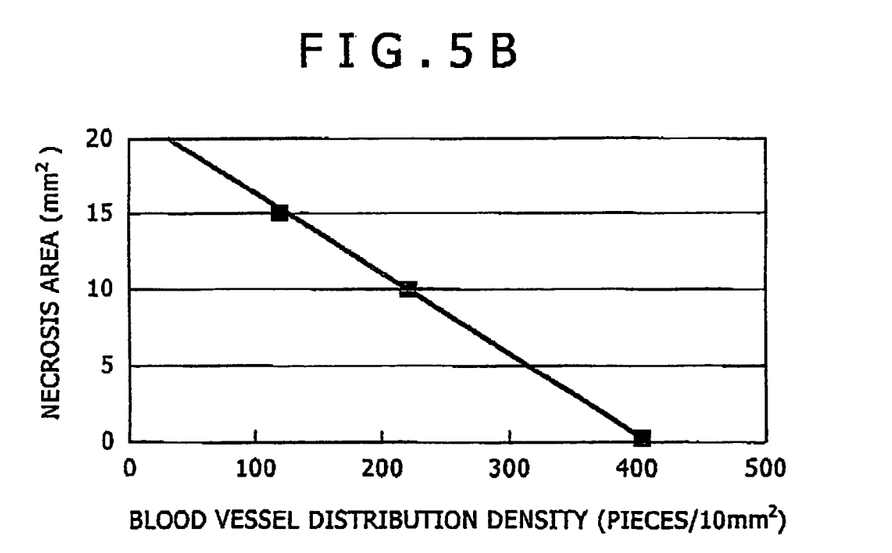

FIG. 5A shows, in a table form, the results of counting the specific numerical values based on the diagrams shown in FIGS. 4A-4C. In addition, FIG. 5B is a graph illustrating the data in the table shown in FIG. 5A. In the FIG. 5B graph, blood vessel distribution density is set forth along the horizontal axis and the necrosis area is set forth along the vertical axis.

As is seen from FIGS. 5A and 5B, in the case where the output of laser light is controlled so that the temperature at the irradiated portion will be a predetermined temperature, a proportional relationship exists between the blood vessel distribution density in a living body and the necrosis area. In view of this characteristic, the target temperature calculation unit 301 utilizes the proportional relationship between the blood vessel distribution density and the necrosis area in calculating the target temperature.

4.2 Calculation Method of Target Temperature

A specific example of a method of calculating a target temperature will be described below using FIG. 5B. FIG. 5B shows that where the target necrosis area is 10 mm² and the output of laser light is controlled so that the temperature at the irradiated portion will be 34° C., a living body with a blood vessel distribution density of 226 pieces/mm² leads to realization of a necrosis area of 10 mm².

With this case as a reference, the target temperature T necessary to realize the target necrosis area $S_0$ (=10 mm²) can be obtained according to the following "temperature calibration formula":

$$T = T\text{cool} + (T_0 - T_{cool}) \times \rho/\rho_0$$

where $T_0$: temperature of irradiated portion used as reference=34° C.

Tcool: temperature of cooling water=20° C.

$\rho_0$: blood vessel distribution density used as reference=226 pieces/mm²

$\rho$: blood vessel distribution density of living body.

Therefore, where the blood vessel distribution density in a living body is 122 pieces/mm², $$T = 20 + (34-20) \times 122/226 = 28°\text{ C.}$$

Thus, to realize a necrosis area of 10 mm² by applying the thermal therapy to a living body having the blood vessel distribution density shown in FIG. 4A, the target temperature T for the irradiated portion is set to 28° C.

Besides, where the blood vessel distribution density in a living body is 408 pieces/mm², $$T = 20 + (34-20) = 408/226 = 45°\text{ C.}$$

Thus, to realize a necrosis area of 10 mm² by applying the thermal therapy to a living body having the blood vessel distribution density shown in FIG. 4C, the target temperature T for the irradiated portion is set to 45° C.

5. Operational Control Using the Energy Irradiation Device

Figure 6:
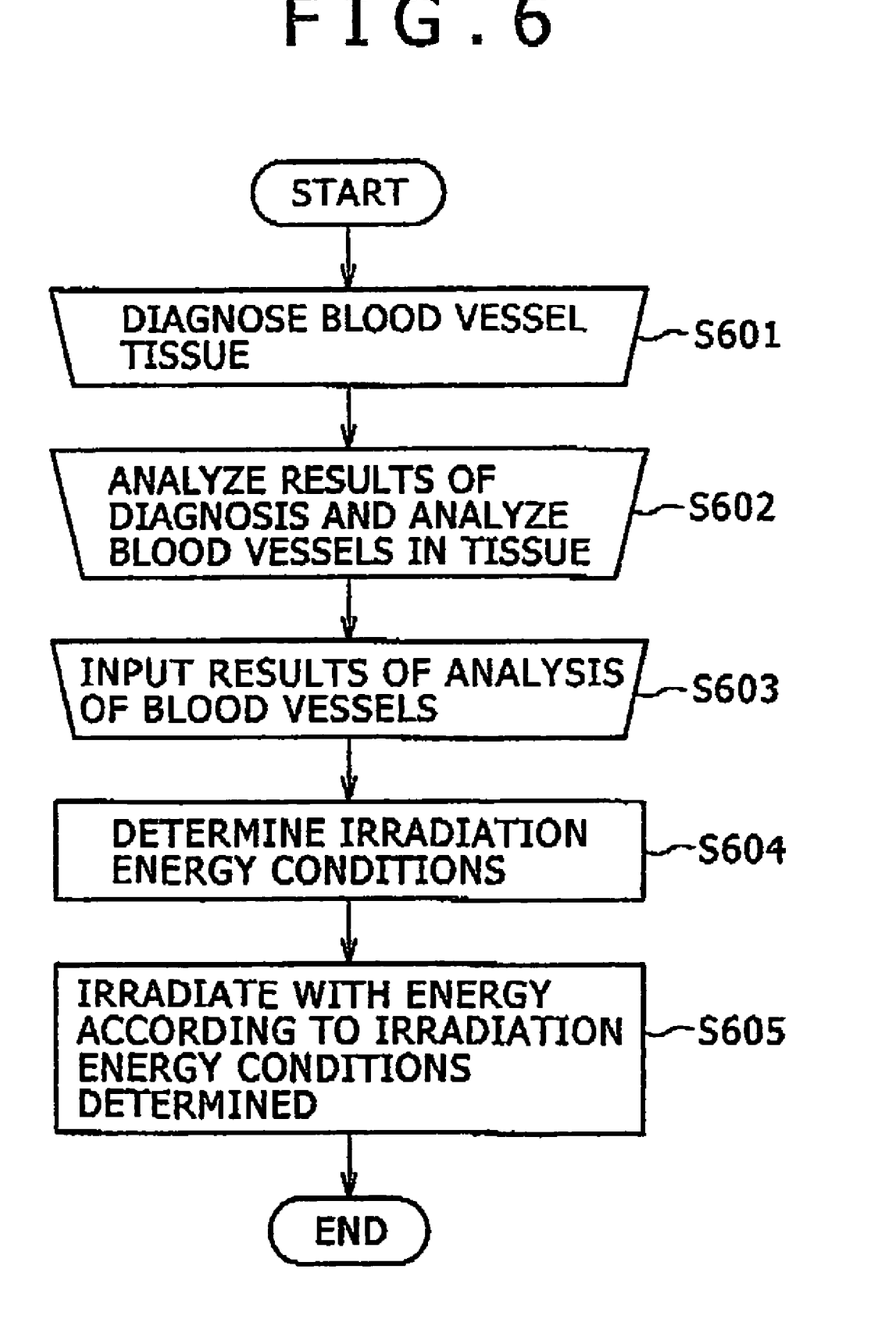
FIG. 6 is an example of a program control carried out during operation of the energy irradiation device.

One example of the operational control associated with the use or operation of the energy irradiation device is described below with reference to FIG. 6. In step S601, the blood vessel tissue at the irradiated portion in a living body is diagnosed. Specifically, the blood vessel tissue is diagnosed by using an ultrasonic imaging and diagnosing device with an ultrasonic transducer connected thereto. It is to be understood, however, that the diagnosing method is not particularly limited in this regard, inasmuch as the blood vessel distribution density can be calculated or determined in other ways. Also, in performing diagnosis, a contrast medium or the like may be used so that an image emphasizing the blood vessel tissues can be obtained.

In step S602, the results of diagnosis are analyzed, and the blood vessel distribution density in the blood vessel tissue is calculated. In step S603, the blood vessel distribution density thus calculated or determined is inputted to the irradiation output controller 102 through the input device 101 shown by way of example in FIG. 1.

In step S604, the target temperature for the irradiated portion is calculated, and then an energy quantity necessary for realizing that target temperature is calculated or determined. In step S605, a living body is irradiated with the calculated or determined quantity of the energy.

Thereafter, the output of the energy is controlled so that the temperature at the irradiated portion will be the target temperature calculated in step S604.

As is clear from the above description, according to this embodiment, the correlation between information on bloodstream quantity and necrosis area in the case of energy irradiation so that the irradiated portion will be brought to a predetermined temperature is preliminarily obtained, the "information on bloodstream quantity" in a living body and a target necrosis area are both inputted at the time of actually performing thermal therapy. By using the correlation, it is possible to determine the temperature to which the temperature of the irradiated portion should be brought by controlling the output of the energy.

As a result, it is possible to apply an appropriate thermal therapy to a lesion portion while generally negating the influences of the "bloodstream quantity in blood vessel tissue"

which differs for different living bodies, thus permitting realization of a desired necrosis area by heating at a desired temperature.

In the first embodiment described above, the blood vessel tissue is diagnosed and the blood vessel distribution density is calculated by analyzing the diagnosis results using an arrangement not connected to the energy irradiation device. The blood vessel distribution density thus calculated is inputted through the input device (e.g., manually by an operator). However, the present invention is not particularly limited in this regard.

For example, an alternative may be adopted in which an ultrasonic transducer is attached to the emission unit of the energy irradiation device, and a blood vessel distribution density measuring device such as an ultrasonic diagnosing device for calculating the blood vessel distribution density on the basis of a reflective echo received by the ultrasonic transducer is connected to the irradiation output controller.

Figure 7:
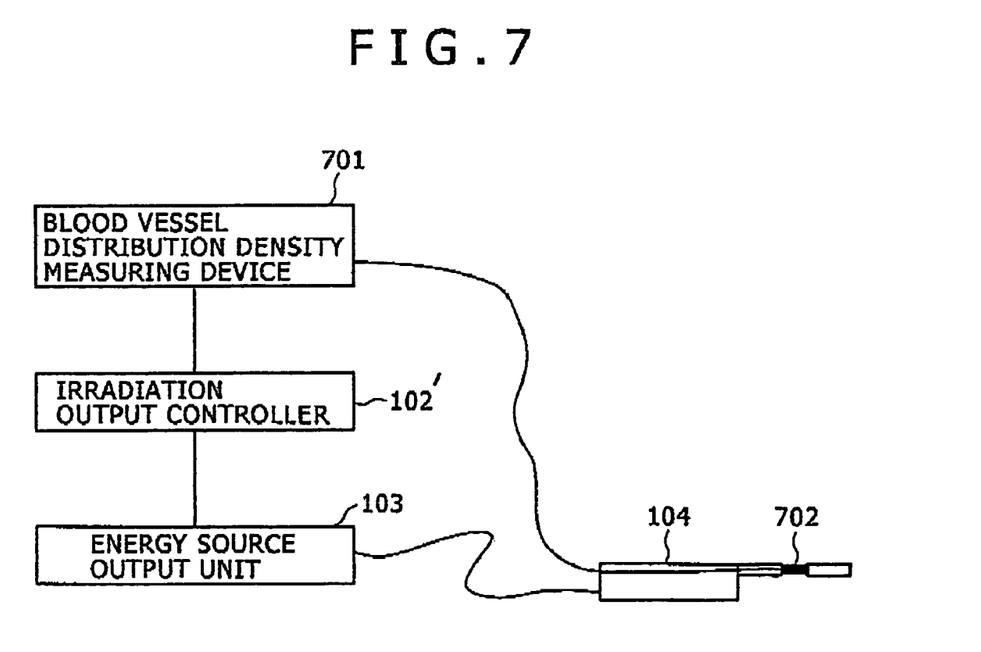
FIG. 7 is a schematic illustration of features forming the energy irradiation device disclosed herein according to a second embodiment.

FIG. 7 schematically illustrates an alternative embodiment of the energy irradiation device along the lines discussed above. This second embodiment of the energy irradiation device utilizes an internal tissue measuring means for measuring a condition of the tissue in the predetermined living body, and a bloodstream quantity calculation means that calculates information about the bloodstream quantity (e.g., blood vessel distribution density) in the living body based on a signal outputted from the internal tissue measuring means. Thus, energy irradiation device includes an ultrasonic transducer 702 attached to the emission unit 104 of the energy irradiation device. Before irradiation with energy, the ultrasonic transducer 702 is operated in the direction of the irradiated portion, and the reflective echo received is inputted to a blood vessel distribution density measuring device 701. The blood vessel distribution density measuring device 701 calculates the blood vessel distribution density, based on the reflective echo inputted thereto, and then transmits the blood vessel distribution density to the irradiation output controller 102'. In this way, the blood vessel distribution density is inputted automatically.

With this arrangement, the irradiation output controller 102' is able to calculate an appropriate target temperature according to the blood vessel distribution density, and irradiation with an appropriate quantity of energy can be realized, in the same manner as in the first embodiment.

In the first and second embodiments described above, an appropriate target temperature to be obtained at the irradiated portion is calculated, and then the control (feedback control) of the energy output is so controlled as to attain the target temperature. However, the present invention is not particularly limited in this regard.

For example, an alternative may be adopted in which the relationship between blood vessel distribution and necrosis area in the case of energy irradiation at a predetermined wattage for a predetermined time is preliminarily obtained, and a wattage and an irradiation time are calculated or determined directly when the blood vessel distribution density of a living body and a target necrosis area are inputted. This alternative is described below in more detail.

1. Energy Irradiation Device

The features associated with the energy irradiation device according to this third embodiment are the same as those associated with the first and second embodiments described above and so a detailed description of the energy irradiation device is not repeated here.

2. Emission Unit

The emission unit in the energy irradiation device according to this third embodiment is basically the same as the emission unit described above in connection with the first and second embodiments. It should be noted, however, that in the energy irradiation device according to this embodiment, the quantity of energy to be outputted is directly obtained by calculation, and the feedback of the temperature measured at the irradiated portion is unnecessary, so that a temperature sensor is not a required component. It is also to be noted here, however, that the temperature sensor can be provided and used for a monitoring purpose, since it is necessary to monitor the results of measurement by the temperature sensor at the time of thermal therapy.

3. Irradiation Output Controller

Figure 8:
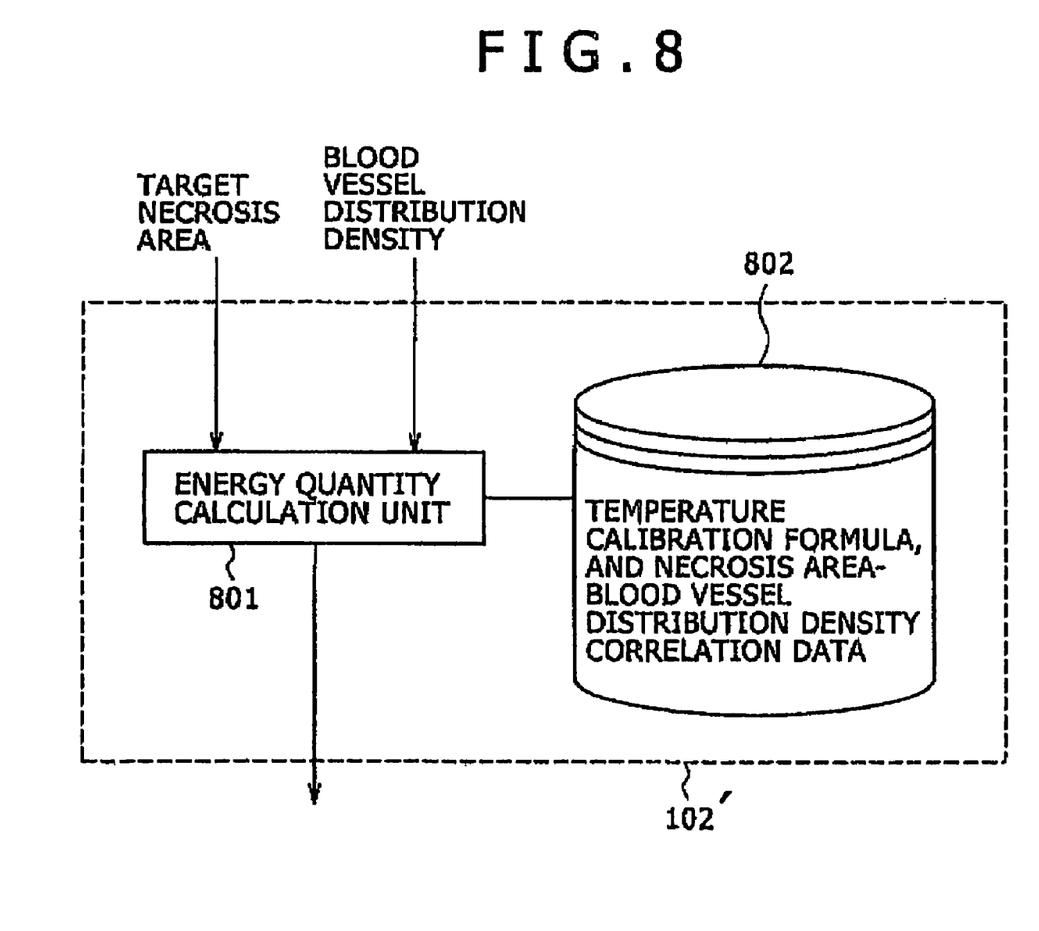
FIG. 8 is a schematic illustration of features forming the irradiation output controller 102 of the energy irradiation device according to another embodiment.

FIG. 8 illustrates features associated with the irradiation output controller 102' forming a part of the energy irradiation device according to this embodiment. The irradiation output controller 102' includes an energy quantity calculating unit 801 (energy quantity calculating means) which calculates or determines the quantity of energy to be outputted (wattage and time in the example where the energy is laser light), based on a target necrosis area and a blood vessel distribution density which are inputted, and with reference to the "energy quantity calibration formula" and the "target necrosis area-blood vessel distribution density correlation data" which are stored in a data storage 802 (storage means) such as a hard disk. Details associated with the calculation method will be described in more detail below. The target necrosis area and the blood vessel distribution density to be used in the energy quantity calculation unit 801 are inputted to the irradiation output controller (e.g., 102, 102') through an input device (e.g., 101) by the operator for instance.

4. Calculation Method in Energy Quantity Calculation Unit

An example of the method of calculating the energy quantity in the energy quantity calculation unit 801 (energy quantity calculation means) is described below.

4.1 Relationship between Blood Vessel Distribution Density and Necrosis Area

Figure 9A:
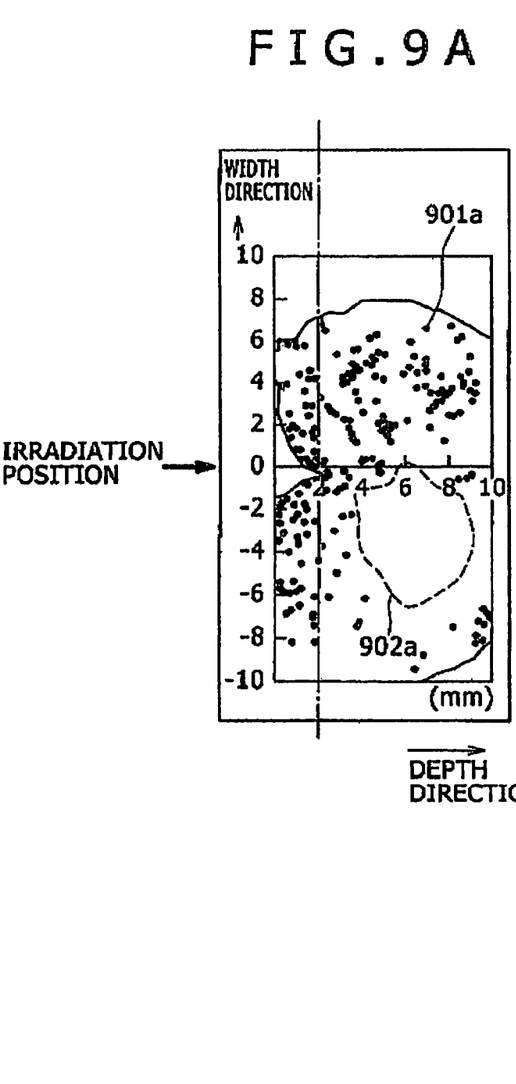
FIGS. 9A-9C are diagrams visualizing the correlation between blood vessel distribution density and necrosis area during irradiation of a living body with laser light at a predetermined wattage (10 W) for a predetermined time (three minutes).
Figure 9B:
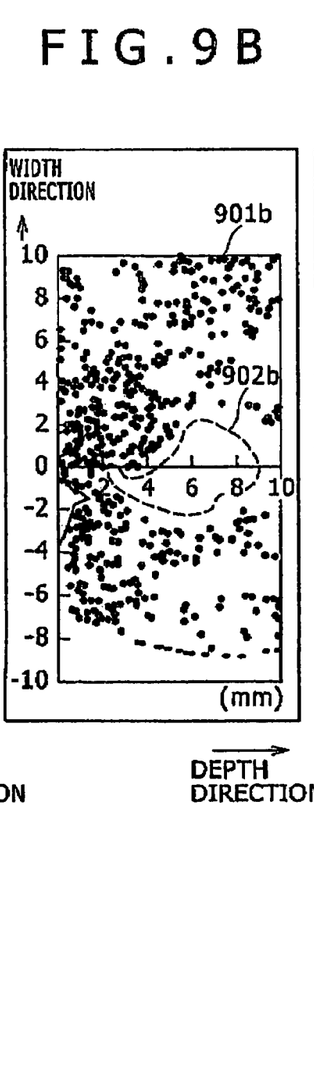
Figure 9C:
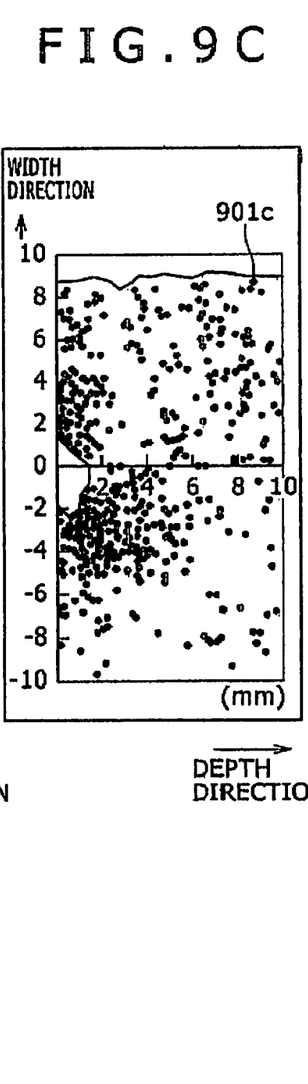

FIGS. 9A-9C are diagrams visualizing the correlation between blood vessel distribution density and necrosis area in the case where living bodies are irradiated with laser light at a predetermined wattage (10 W) for a predetermined time (three minutes) (the energy quantity outputted at this wattage for this time will hereinafter be referred to as "reference output").

In FIGS. 9A-9C, blood vessels are denoted by reference characters 901a-901c, and the blood vessel distribution density increases in the direction from FIG. 9A toward FIG. 9C. The portions necrosed by irradiation with laser light are denoted by reference characters 902a and 902b.

FIG. 9A shows that when a living body with a low blood vessel distribution density was irradiated with laser light at 10 W for three minutes, the portion 902a was necrosed. On the other hand, FIG. 9C shows that when a living body with a high blood vessel distribution density was irradiated with laser light at 10 W for three minutes, no portion was necrosed. Further, FIG. 9B shows that when a living body with an intermediate level of blood vessel distribution density was irradiated with laser light at 10 W for three minutes, the portion 902b was necrosed.

It is thus understood from the illustrations in FIGS. 9A-9C that even if laser light is outputted at the same wattage for the same period of time, the effect of thermal therapy (the size or extent, if any, of the necrosis area) on living bodies differs relatively significantly based on differences in the blood vessel distribution density of the living body.

Figure 10A:
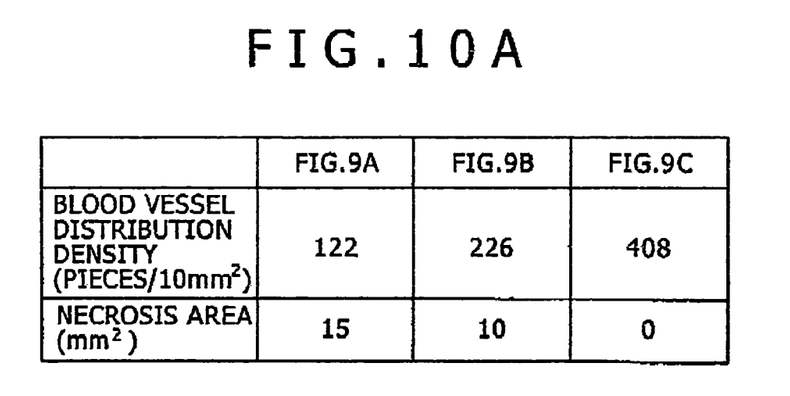
FIGS. 10A and 10B set forth in a table and a graph respectively the correlation between blood vessel distribution density and necrosis area.
Figure 10B:
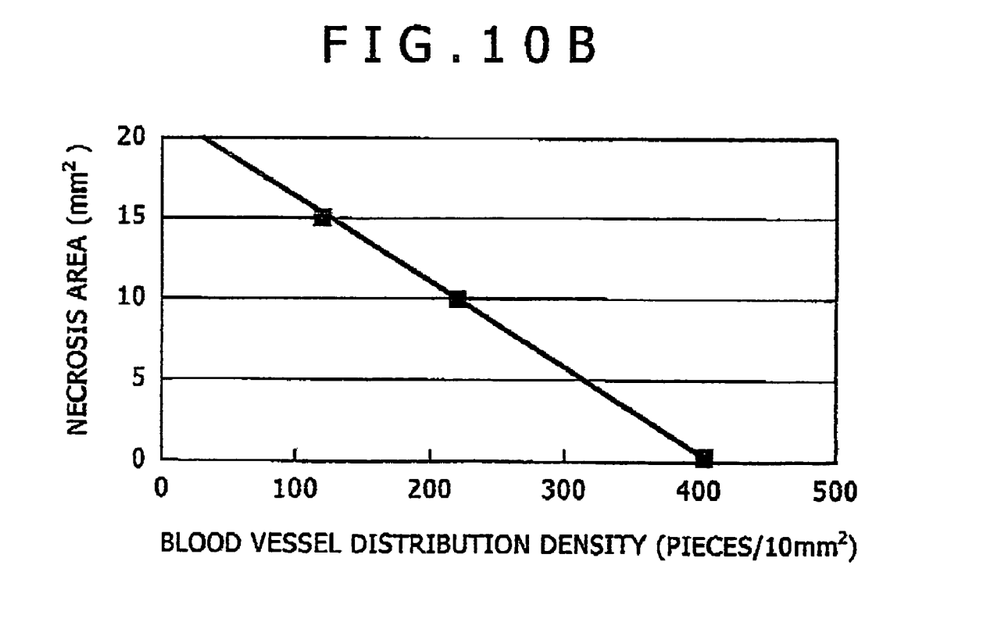

FIG. 10A shows, in table form, the results of counting the specified numerical values, based on the diagrams shown in FIGS. 9A-9C. FIG. 10B illustrates the results in FIG. 10A in a graph. In the graph, the blood vessel distribution density is shown along the horizontal axis and the necrosis area is shown along the vertical axis.

As is seen from FIGS. 10A and 10B, in the case where laser light is outputted at 10 W for three minutes, a proportional relationship exists between the blood vessel distribution density in the living body and the necrosis area. In view of this characteristic, the proportional relationship between the blood vessel distribution density and the necrosis area is utilized in calculating the quantity of energy to be outputted in the energy quantity calculation unit 801.

4.2 Calculation Method of Energy Quantity

With reference to FIG. 10B, the method of calculating the energy quantity is described below by way of a specific example. FIG. 10B shows that, where a target necrosis area is 10 mm² and where laser light is outputted at 10 W for three minutes, a living body with a blood vessel distribution density of 226 pieces/mm² leads to realization of a necrosis area of 10 mm².

Taking this a reference, the quantity E of energy necessary for realizing a target necrosis area S0 (=10 mm²) can be obtained according to the following "energy quantity calibration formula":

$$E=E_0 \times \rho/\rho_0$$

where $E_0$: reference output=10 W, three minutes $\rho_0$: blood vessel distribution density used as reference=226 pieces/mm²

$\rho$: blood vessel distribution density in living body.

Therefore, in the case where the blood vessel distribution density is 122 pieces/mm², $$E=E_0 \times 122/226 = 0.54 E_0.$$

Thus, to realize a necrosis area of 10 mm² by applying the thermal therapy to a living body having the blood vessel distribution density shown in FIG. 9A, the energy output is set to a value of 0.54 times the reference output. Alternatively, where the blood vessel distribution density in a living body is 408 pieces/mm², $$E=E0 \times 408/226 = 1.81 E_0.$$

Namely, in order to realize a necrosis area of 10 mm² by applying the thermal therapy to a living body having the blood vessel distribution density shown in FIG. 9C, the energy output is set to a value of 1.81 times the reference output.

5. Operational Control Using the Energy Irradiation Device

Figure 11:
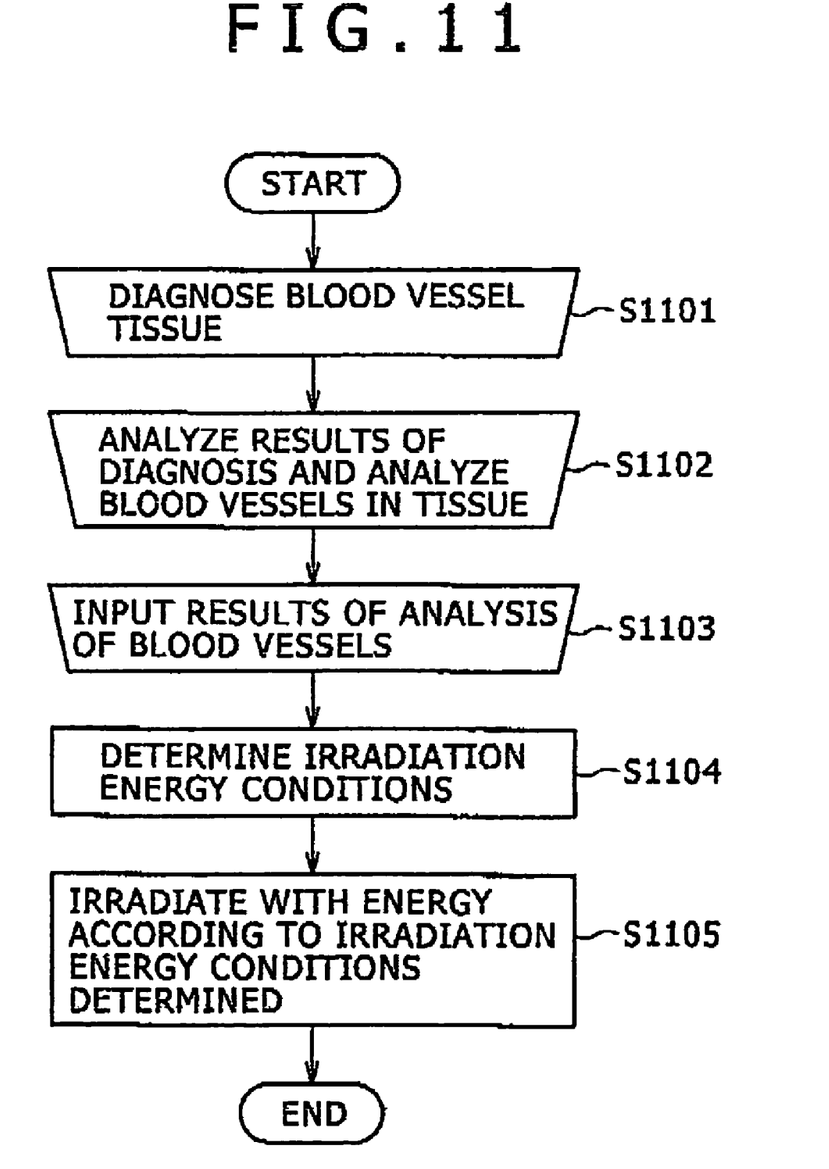
FIG. 11 is an example of a program control carried out during operation of the energy irradiation device.

An example of the operational control associated with the use or operation of the energy irradiation device is described below with reference to FIG. 11. In step S1101, the blood vessel distribution at the irradiated portion of a living body is diagnosed. Specifically, the blood vessel tissue is diagnosed by use of an ultrasonic imaging and diagnosing device with an ultrasonic transducer connected thereto. It should be noted here, however, that the diagnosing method is not particularly limited, inasmuch as the blood vessel distribution density can be determined or calculated by another method. In addition, in performing diagnosis, a contrast medium or the like may be used so that an image emphasizing the blood vessel tissues can be obtained.

In step S1102, the results of the diagnosis are analyzed, and the blood vessel distribution density in the blood vessel tissue is calculated. In step S1103, the blood vessel distribution density thus calculated is inputted to the irradiation output controller (e.g., 102, 102') through the input device (e.g., 101). In step S1104, the quantity of energy to be outputted is calculated. In step S1105, the living body is irradiated with the calculated quantity of energy.

As is clear from the above description, according to this embodiment, it is possible to obtain an incidental effect of simplifying the control device as compared with the first and second embodiments (the control device is composed of an open-loop control in this embodiment, as opposed to the feedback control in the first and second embodiments), while enjoying the same effect as in the first and second embodiments.

Figure 12:
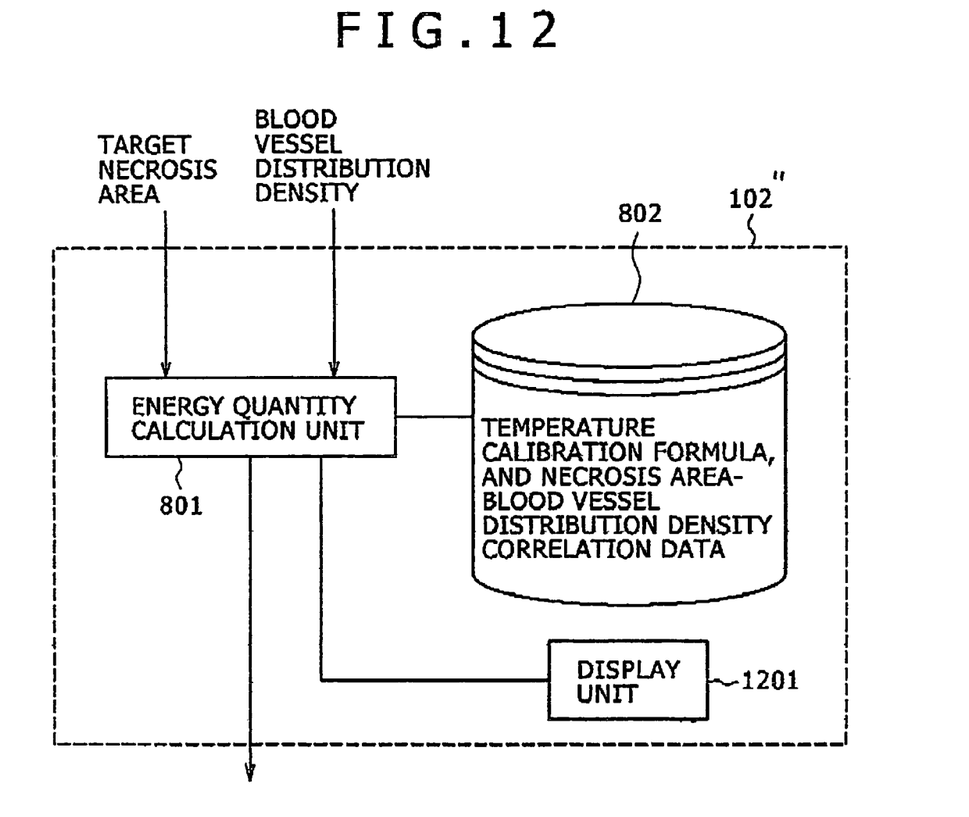
FIG. 12 is a schematic illustration of an irradiation output controller 102″ forming part of an energy irradiation device disclosed herein according to a fourth embodiment.

In the third embodiment described above, the quantity of energy to be outputted is calculated directly, and the setting of specific wattage and irradiation time has not been referred to. However, in relation to the setting of a wattage and an irradiation time, a configuration may be adopted in which, for example, after the quantity of energy to be outputted is calculated, combinations of wattage and irradiation time corresponding to the energy quantity are displayed, and one of the combinations is selected by the operator. FIG. 12 is a schematic illustration of an irradiation output controller 102" in an energy irradiation device according to such an alternative embodiment. The components in this fourth embodiment corresponding to those in the third embodiment described above are denoted by the same reference numerals as used above.

Figure 13:
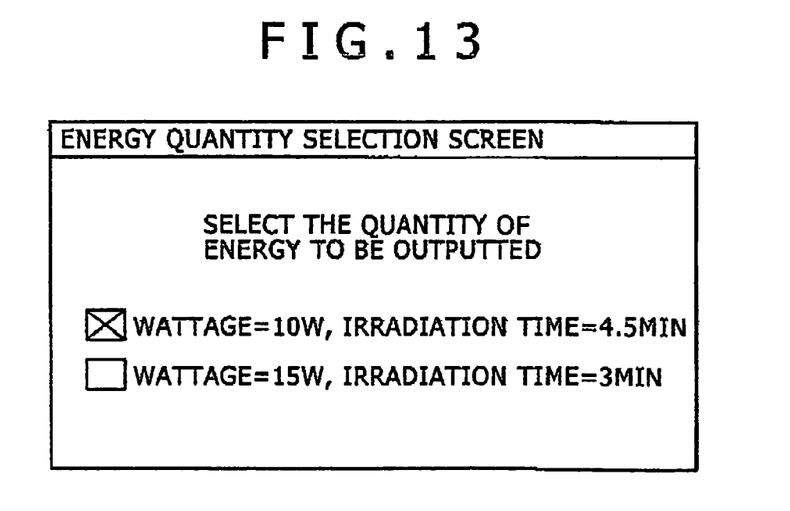
FIG. 13 is a schematic illustration of an example of a display screen displayed on a display unit 1201.

In FIG. 12, a display unit displays the combinations of wattage and irradiation time corresponding to the energy quantity calculated in the energy quantity calculation unit. FIG. 13 is a diagram showing an example of a display screen displayed on the display unit 1201. The operator selects a desired combination on the screen shown in FIG. 13, whereby the energy quantity can be set.

Naturally, the third and fourth embodiments described above can be realized based on the configuration of the energy irradiation device described in both the first and second embodiments above.

In the third and fourth embodiments described above, the energy quantity is calculated based on the correlation between blood vessel distribution density and necrosis area. However, the invention is not particularly limited in this regard. For example, use may be made of other information on bloodstream quantity, such as blood amount and blood flow rate in the blood vessel tissue.

In the embodiments of the energy irradiation device described above, the energy irradiation device is positioned at an appropriate position relative to the living body to be irradiated, and the living body is irradiated with the quantity of energy determined based on the inputted target necrosis area and information about the bloodstream quantity (e.g., blood vessel distribution density), and with reference to the correlating data stored in the data storage. Of course, depending upon the particular embodiment and implementation, the target necrosis area and information about the bloodstream quantity can be inputted at any time (e.g., before or after) relative to when the energy irradiation device is positioned at an appropriate position relative to the living body to be irradiated In the above-described embodiments, the blood vessel distribution density is obtained by applying ultrasonic imaging and diagnosis to the reflective echo coming from the ultrasonic transducer. It is to be appreciated that the invention is not particularly limited in this manner. For example, the blood vessel distribution may be obtained by use of MRI, CT or the like.

The principles, preferred embodiments and modes of operation have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An energy irradiation device for medical use to irradiate a living body with energy, comprising:
    storage means for storing data providing correlations between information about bloodstream quantities and an amount of tissue necrosed in different living bodies differing in bloodstream quantity that are irradiated with a predetermined quantity of the energy; and
    calculation means for calculating the quantity of the energy with which to irradiate a predetermined living body based on the data stored in the storage means, information about the bloodstream quantity in the predetermined living body, and an amount of tissue to be necrosed in the predetermined living body.

2. The energy irradiation device according to claim 1, wherein the data stored in the storage means provides for a quantity of the energy being controlled so that the temperature of a surface of the predetermined living body to be irradiated with the energy will be constant.

3. The energy irradiation device according to claim 2, further comprising temperature measuring means for measuring the temperature of the surface of the predetermined living body to be irradiated with the energy.

4. The energy irradiation device according to claim 3, wherein said calculation means further comprises:
    target temperature calculation means for calculating a target temperature of the surface of the predetermined living body to be irradiated with the energy based on the data stored in the storage means, the information about the bloodstream quantity in the predetermined living body, and the amount of the tissue to be necrosed in the predetermined living body; and
    energy quantity calculation means for calculating the quantity of the energy based on the temperature measured by the temperature measuring means and the target temperature calculated by the target temperature calculation means.

5. The energy irradiation device according to claim 4, wherein the target temperature calculation means calculates the target temperature T according to $T=Tcool+(T_0-Tcool)\times \rho/\rho_0$, where $\rho_0$ is the information about the bloodstream quantities constituting part of the data stored in the storage means, $\rho$ is the information about the bloodstream quantity in the predetermined living body, $T_0$ is the temperature of the surface irradiated with the energy when the data is acquired, and Tcool is the temperature of cooling water for cooling an energy irradiation port.

6. The energy irradiation device according to claim 1, wherein the energy is laser light.

7. The energy irradiation device according to claim 1, wherein the data stored in the storage means provides for the quantity of the energy to be constant.

8. The energy irradiation device according to claim 7, wherein the calculation means calculates the quantity E of the energy with which to irradiate the predetermined living body according to $E=E_0\times\rho/\rho_0$, where $\rho_0$ is the information about the bloodstream quantities constituting part of the data stored in the storage means, $\rho$ is the information about the bloodstream quantity in the predetermined living body, and $E_0$ is the quantity of the energy used for irradiation therewith when the data is acquired.

9. The energy irradiation device according to claim 8, wherein the energy is laser light.

10. The energy irradiation device according to claim 1, further comprising a display adapted to display different combinations of wattage and irradiation time providing the quantity of the energy calculated by the calculation means to permit operator selection of one of the displayed combinations.

11. The energy irradiation device according to claim 1, wherein the information about the bloodstream quantities that is correlated to amount of tissue necrosed in different living bodies is blood vessel distribution density.

12. The energy irradiation device according to claim 1, further comprising:
    internal tissue measuring means for measuring a condition of the tissue in the predetermined living body; and
    bloodstream quantity calculation means for calculating the information about the bloodstream quantity in the predetermined living body based on a signal outputted from the internal tissue measuring means.

* * * * *